(12) United States Patent
Pinsky et al.

(10) Patent No.: US 8,446,582 B2
(45) Date of Patent: May 21, 2013

(54) SYSTEM AND METHOD FOR ANALYZING FLUIDS

(75) Inventors: Niv Pinsky, Kibbutz Afikim-Doar-Na Emek HaYarden (IL); Gil Katz, Kibbutz Afikim-Doar-Na Emek HaYarden (IL); Benjamin Sabbah, Haifa (IL); Martin I. Kutscher, Moshav Mishmar HaYarden-Doar-Na Galil Elyon (IL); Moran Sarig, Kibbutz Afikim-Doar-Na Emek HaYarden (IL); Ziv Merchav, Kiryat-Bialik (IL); Alon Gilboa, Kibbutz Ashdot Yaakov-Doar-Na Emek HaYarden (IL)

(73) Assignee: Afimilk Agricultural Cooperative Ltd., Kibutz Afikim (IL)

( * ) Notice: Subject to any disclaimer, the term of this patent is extended or adjusted under 35 U.S.C. 154(b) by 561 days.

(21) Appl. No.: 12/602,157

(22) PCT Filed: May 26, 2008

(86) PCT No.: PCT/IL2008/000710
§ 371 (c)(1),
(2), (4) Date: Jun. 29, 2010

(87) PCT Pub. No.: WO2008/146276
PCT Pub. Date: Dec. 4, 2008

(65) Prior Publication Data
US 2010/0285523 A1    Nov. 11, 2010

Related U.S. Application Data

(60) Provisional application No. 60/924,809, filed on May 31, 2007.

(51) Int. Cl.
*G01J 3/42* (2006.01)
(52) U.S. Cl.
USPC .......................................... 356/319
(58) Field of Classification Search ............. 356/319
See application file for complete search history.

(56) References Cited

U.S. PATENT DOCUMENTS

| 1,915,267 A | 6/1933 | Bigelow |
| 4,667,188 A | 5/1987 | Schwartz |

(Continued)

FOREIGN PATENT DOCUMENTS

| CN | 200944242 | 9/2007 |
| CN | 101114372 | 1/2008 |

(Continued)

OTHER PUBLICATIONS

Response Dated Mar. 29, 2011 to Office Action of Sep. 1, 2010 From the Israeli Patent Office Re.: Application No. 173604.

(Continued)

*Primary Examiner* — Tu Nguyen
(74) *Attorney, Agent, or Firm* — Pearl Cohen Zedek Latzer, LLP

(57) ABSTRACT

A spectrometric sensor for measuring a spectra value of a flowing fluid. The spectrometric sensor comprises a light source for emitting a first light flux toward a sample of the flowing fluid, a light detector for measuring a first intensity of a reflection of the first light flux from the flowing fluid and a second intensity of a second light flux received via the flowing fluid, and a control unit configured for generating at least one spectra value according to at least one of the first and second intensities.

22 Claims, 5 Drawing Sheets

U.S. PATENT DOCUMENTS

| | | | |
|---|---|---|---|
| 5,006,676 | A | 4/1991 | Bogut et al. |
| 6,104,294 | A | 8/2000 | Andersson et al. |
| 6,115,679 | A | 9/2000 | Rutter et al. |
| 6,129,686 | A | 10/2000 | Friedman |
| 6,348,665 | B1 | 2/2002 | Ohashi et al. |
| 6,536,377 | B2 | 3/2003 | Beaver |
| 6,616,607 | B2 | 9/2003 | Hashimoto et al. |
| 7,602,302 | B2 | 10/2009 | Hokuf et al. |
| 7,705,736 | B1 | 4/2010 | Kedziora |
| 2001/0050062 | A1 | 12/2001 | Isley et al. |
| 2002/0198441 | A1* | 12/2002 | Tsenkova ............... 600/310 |
| 2003/0069515 | A1 | 4/2003 | Theelen et al. |
| 2003/0098969 | A1* | 5/2003 | Katz et al. ............. 356/73 |
| 2004/0179194 | A1 | 9/2004 | Schmilovitch et al. |
| 2006/0022833 | A1 | 2/2006 | Ferguson et al. |
| 2007/0197885 | A1* | 8/2007 | Mah et al. .............. 600/310 |
| 2008/0036610 | A1 | 2/2008 | Hokuf et al. |
| 2008/0125670 | A1 | 5/2008 | Signorini et al. |
| 2008/0147458 | A1 | 6/2008 | Yamazaki et al. |
| 2008/0204255 | A1 | 8/2008 | Flexer et al. |
| 2009/0056637 | A1 | 3/2009 | Gustafsson |
| 2010/0030036 | A1 | 2/2010 | Mottram et al. |

FOREIGN PATENT DOCUMENTS

| | | |
|---|---|---|
| DE | 249974 | 9/1987 |
| DE | 4118168 | 1/1993 |
| DE | 69501446 | 8/1998 |
| DE | 69629869 | 7/2004 |
| DE | 202005015781 | 3/2006 |
| EP | 0743043 | 11/1996 |
| EP | 0808567 | 11/1997 |
| EP | 1000535 | 5/2000 |
| EP | 1169917 | 1/2002 |
| EP | 1191325 | 3/2002 |
| EP | 1191326 | 3/2002 |
| EP | 1199027 | 4/2002 |
| EP | 1212939 | 6/2002 |
| EP | 1839621 | 10/2007 |
| FR | 2759541 | 8/1998 |
| FR | 2878430 | 6/2006 |
| GB | 2221161 | 1/1990 |
| GB | 2257886 | 1/1993 |
| IE | 20040051 | 9/2005 |
| JP | 06-141385 | 5/1994 |
| JP | 10-295212 | 11/1998 |
| JP | 2003-189751 | 7/2003 |
| JP | 2004-275124 | 7/2004 |
| JP | 2004-337093 | 12/2004 |
| JP | 2006-075090 | 3/2006 |
| JP | 2008-022760 | 2/2008 |
| JP | 2010-033329 | 2/2010 |
| RU | 2060499 | 6/1996 |
| WO | WO 00/33028 | 6/2000 |
| WO | WO 01/19170 | 3/2001 |
| WO | WO 2004/066720 | 8/2004 |
| WO | WO 2005/067702 | 7/2005 |
| WO | WO 2007/091246 | 8/2007 |
| WO | WO 2008/124481 | 10/2008 |
| WO | WO 2008/146276 | 12/2008 |
| WO | WO 2010/066429 | 6/2010 |
| WO | WO 2010/099800 | 9/2010 |

OTHER PUBLICATIONS

Summary of Official Action Dated Mar. 30, 2010 From the Patent Office of the Russian Federation Re.: Application No. 2009-7024590.
Response Dated May 13, 2010 to Office Action of Dec. 14, 2009 From the Israeli Patent Office Re.: Application No. 173604.
Office Action Dated Sep. 1, 2010 From the Israeli Patent Office Re.: Application No. 173604 and Its Translation Into English.
Examination Report Dated Oct. 11, 2010 From the Intellectual Property Office of New Zealand Re. Application No. 581254.
Response Dated Apr. 6, 2011 to Examination Report of Oct. 11, 2010 From the Intellectual Property Office of New Zealand Re. Application No. 581254.
Examination Report Dated May 24, 2011 From the Intellectual Property Office of New Zealand Re. Application No. 581254.
Translation of Office Action Dated May 11, 2011 From the State Intellectual Property Office of People's Republic of China Re. Application No. 200780004737.9.
Communication Pursuant to Rules 70(2) and 70a(2) EPC Dated May 9, 2011 From the European Patent Office Re. Application No. 07706091.1.
Supplementary European Search Report and the European Search Opinion Dated Apr. 20, 2011 From the European Patent Office Re. Application No. 07706091.1.
Response Dated Jun. 22, 2010 to Summary of Official Action of Mar. 30, 2010 From the Patent Office of the Russian Federation Re.: Application No. 2009-7024590.
Supplementary European Search Report and the European Search Opinion Dated Jul. 6, 2010 From the European Patent Office Re. Application No. 06733333.6.
Eizenbod et al. Article in Hebrew ["Developments in Recognition of Estrus in Cows", Research and Deed, 9: 39-43, 1987. Abstract.
Official Action Dated Oct. 28, 2010 From the US Patent and Trademark Office Re. U.S. Appl. No. 12/149,576.
Official Action Dated Mar. 29, 2011 From the US Patent and Trademark Office Re. U.S. Appl. No. 12/149,576.
International Preliminary Report on Patentability Dated Mar. 10, 2009 From the International Bureau of WIPO Re.: Application No. PCT/IL2007/000148.
International Preliminary Report on Patentability Dated Aug. 14, 2009 From the International Preliminary Examining Authority Re.: Application No. PCT/IL2008/000710.
International Search Report Dated Oct. 2, 2008 From the International Searching Authority Re.: Application No. PCT/IL2008/000613.
International Search Report Dated Oct. 2, 2008 From the International Searching Authority Re.: Application No. PCT/IL2008/000710.
International Search Report Dated Oct. 29, 2008 From the International Searching Authority Re.: Application No. PCT/IL07/00148.
Office Action Dated May 14, 2009 From the Israeli Patent Office Re.: Application No. 173604 and Its Translation Into English.
Written Opinion Dated Oct. 2, 2008 From the International Searching Authority Re.: Application No. PCT/IL2008/000613.
Written Opinion Dated Oct. 2, 2008 From the International Searching Authority Re.: Application No. PCT/IL2008/000710.
Written Opinion Dated Oct. 29, 2008 From the International Searching Authority Re.: Application No. PCT/IL07/00148.
Esslemont et al. "Oestrous Behaviour in a Herd of Dairy Cows", The Veterinary Record, 99: 472-475, 1976. Abstract.
Livshin et al. "Lying Behaviour of Dairy Cows Under Different Housing Systems and Physiological Conditions", Proc. Implementation of Precision Agriculture, 2nd ECPLF, Jun. 9-12, Uppsala, Sweden: 305-311, 2005.
Schofield "Oestrus Detection Methods and Oestrous Behaviour of Dairy Cows in Different Environments", Dissertation Abstracts International B, Sciences and Engineering, 49: 2432, 1989. Abstract.
Office Action Dated Dec. 14, 2009 From the Israeli Patent Office Re.: Application No. 173604 and Its Translation Into English.
Preliminary Amendment Dated Jan. 11, 2010 From the US Patent and Trademark Office Re.: U.S. Appl. No. 12/149,576.
Phatak "The Detection of Estrus in Dairy Cattle by Monitoring Behavioral Change in Stanchion Barn and Free Stall Housing", PhD Thesis Submitted to the faculty of the Graduate School of the University of Minnesota, 1982.
Response Dated Jan. 27, 2011 to Official Action of Oct. 28, 2010 From the US Patent and Trademark Office Re. U.S. Appl. No. 12/149,576.

* cited by examiner

SYSTEM AND METHOD FOR ANALYZING FLUIDS

RELATED APPLICATIONS

This Application is a National Phase of PCT Patent Application No. PCT/IL2008/000710 having International filing date of May 26, 2008, which claims the benefit of U.S. Provisional Patent Application No. 60/924,809 filed on May 31, 2007. The contents of the above Applications are all incorporated herein by reference.

FIELD OF THE INVENTION

The present invention relates to a device, a system, and a method for fluids analysis and, more particularly, but not exclusively to a device and a method for spectrophotometric analysis of a flowing fluid.

BACKGROUND OF THE INVENTION

Various techniques of spectrophotometry of liquids, such as milk, are already known. In particular, spectrophotometry techniques that are based on measurement of the light transmitted through the liquid and detected by detectors comprising photo diode strips. Such techniques are used, inter alia, for estimating the quality of milk.

In order to estimate the quality of milk, information about various component parts of the milk is acquired and checked. Such information is useful, inter alia, for different aspects of the herd management. The various component parts may include fat, total protein, casein, lactose, somatic cells, blood, progesterone, amino-acids urea, and nucleic acid. The information may be used as an economic indicator of the overall milk quality. For example, the fat and protein content may be used for determining the price that a farmer obtains for per gallon of milk. The information may be used to analyze the diet of the cattle. For example, changes in the fat content may indicate an imbalance in the forage-to-concentrate ratio in the feed, a low total protein level may indicate a dietetic energy deficiency, a somatic cell count and a blood count may be used as diagnostic indicators of a specific clinical state of the cow, fluctuations in lactose content may indicate the presence of mastitis, etc.

Several methods for performing milk analysis are known. For example, the use of near infrared (near IR) spectroscopy for analyzing milk has been known for almost 15 years. In the article "Near Infra-Red Spectroscopy for Dairy Management: Measurement of Unhomogenized Milk Composition" by R. Tsenkova et al., published in Journal of Dairy Science, Vol. 82, pp. 2344-2351, 1999, which is incorporated herein by reference, there is proposed a method whereby the milk content is spectroscopically analyzed in the near IR range of from 400 nm to 2500 nm.

Further descriptions of methods of milk analysis using near IR spectroscopy are given in the articles "Fresh Raw Milk Composition Analysis by Near IR Spectroscopy" by Z. Schmilovitch et al, published in Proceedings of the International Symposium on the Prospects for Automatic Milking, Wageningen, Netherlands, EAAP Publication No. 65, pp. 193-198 (1992), and "Low Cost Near Infra-red Sensor for On-line Milk Composition Measurement" by Z. Schmilovitch et al., published in the Proceedings of the XIV Memorial CIGR World Congress, 2000, Tsukuba, Japan, which are incorporated herein by reference.

A number of known instruments and systems for performing milk analysis using near infrared (Near IR) spectroscopy are also known. For example, U.S. Patent Publication 2006/0092422, published on May 4, 2006, discloses a device for analyzing a non-limpid medium. The device illuminates the medium by at least one light pulse, acquires a spectral and temporal transmission image from the lit medium, and processes the image and derivatives thereof so as to acquire information about the non-limpid medium. The disclosure relates to the analysis of diffusing and absorbing media, for example milk.

Another example of milk analysis is disclosed in International Patent Publication WO/2003/040704, which is incorporated herein by reference, and discloses a near IR spectroscopy fluids analyzing system using a series of light emitting diodes (LEDs), each having a preselected center wavelength as illumination sources. The wavelengths have overlapping spectral widths, such that the measurement covers a broad spectrum. The LEDs sequentially illuminate the fluids sample. Subsequently, the transmission absorbance through the sample and the reflectance or scattering from the sample is measured for the wavelength range of each LED. The measurements are performed using photodetectors. The concentrations of component parts of the fluids are expressed in the form of a polynomial, which is a function of the measured transmitted, reflected intensities, or both, and of empirical coefficients, which are extracted by prior statistical analysis on measured intensities obtained from a large number of test samples having known concentrations of the component.

Though such systems and devices allow the analysis of fluids, such as milk, there is a need for a relatively inexpensive solution that can provide new advanced capabilities for measuring the presences of various component parts of a portion of such as milk.

SUMMARY OF THE INVENTION

According to one aspect of some embodiments of the present invention there is provided a spectrometric sensor for measuring a spectra value of a sample of a flowing fluid. The spectrometric sensor comprises a first light source configured for emitting a first light flux toward the sample, a first light detector configured for measuring a first intensity of a reflection of the first light flux from the sample and a second intensity of a second light flux transmitted through the sample, and a control unit configured for generating at least one spectra value according to at least one of the first and second intensities.

Optionally, the first light source is configured for emitting an ultraviolet light flux centered at ultraviolet wavelength.

Optionally, at least one of the first and second intensity is indicative of a concentration of somatic cells in the sample.

Optionally, the spectrometric sensor further comprises a light calibration unit configured for receiving a portion of the first light flux and adjusting the first light source to emit light at a predefined intensity.

More optionally, the light calibration unit comprises a feedback detector for receiving the portion of light emitted by the first light flux.

More optionally, a light guide guides the portion of light emitted by the first light flux to the feedback detector.

More optionally, the light guide deriving the portion from approximately the center of the first light flux.

Optionally, the spectrometric sensor further comprises a converging lens configured for converging the reflection and the second light flux onto the light detector.

Optionally, the sample comprising milk.

Optionally, the at least one spectra value is used for chemometric analysis of the sample.

Optionally, the control unit is configured for transmitting the at least one spectra value to a central unit.

Optionally, the sample is housed in a sampling chamber.

More optionally, the sampling chamber having first and second transparent portions, the first and second transparent portions, the first and second light fluxes are respectively emitted toward the first and second transparent portion.

Optionally, the at least one spectra value is indicative of a concentration of somatic cells in a sample of the flowing fluid.

Optionally, the spectrometric sensor according to any of the afore mentioned optional embodiment further comprises a thermo-stabilization unit configured for sustaining the first light source in a predefined temperature range, thereby stabilizing the light flux on a predefined intensity.

More optionally, thermo-stabilization unit comprising a heating device, the sustaining is performed using the heating device.

More optionally, the heating device is a heating resistor.

Optionally, the spectrometric sensor according to any of the afore mentioned optional embodiment further comprises the first light source comprising a set of light emitting diodes (LEDs) for emitting a plurality of first light fluxes, the first light detector is configured for measuring a plurality of intensities of at least one of reflections of the plurality of first light fluxes from the sample and a plurality of second light fluxes received via the sample.

More optionally, the control unit is configured for generating the at least one spectra value according to the plurality of intensities.

More optionally, each the LED generates light at a band of wavelengths centered at a different wavelength from the other LEDs.

Optionally, the spectrometric sensor according to any of the afore mentioned optional embodiment further comprises the first light detector is configured for measuring calibration intensity from at least one of a reflection of the first light flux from a calibration fluid and a portion of the second light flux.

More optionally, the control unit is configured for generating the at least one spectra value according to a deviation between the at least one of the first and second intensities and a calibration intensity.

Optionally, the spectrometric sensor according to any of the afore mentioned optional embodiment is part of a device further comprising a second spectrometric sensor having a second light source configured for emitting the second light flux toward the sample, and a second light detector configured for measuring a third intensity of a reflection of the second light flux from the sample and a fourth intensity of the first light flux transmitted through the sample, wherein the control unit configured for generating at least one spectra value according to at least one of the third and fourth intensities.

According to another aspect of some embodiments of the present invention there is provided a device for acquiring spectrometric information from a sample of a flowing fluid, the device comprises a light source configured for emitting a first light flux having a predefined intensity toward the sample, a light detector configured for acquiring a spectrometric measurement from at least one of a reflection of the first light flux from the sample and a portion of a second light flux received via the sample, and a thermo-stabilization unit configured for sustaining the light source in a predefined temperature, thereby stabilizing the intensity of the first light flux on the predefined intensity.

According to another aspect of some embodiments of the present invention there is provided a system for estimating a number of somatic cells in a sample of milk. The system comprises a light source configured for emitting a light flux centered on an ultraviolet (UV) wavelength toward the sample, a light detector configured for generating a measurement according to at least one of a reflection of the light flux from the sample and a portion of the light flux received via the sample, and a control unit for estimating the number of somatic cells according to the measurement.

Optionally, the system further comprises a sampling chamber configured for containing the sample.

Optionally, the milk is flowing milk.

Optionally, the center UV wavelength is between 365 nanometer and 400 nm nanometer.

According to another aspect of some embodiments of the present invention there is provided a method for estimating a number of somatic cells in a sample of milk. The method comprises a) emitting a light flux centered on an ultraviolet (UV) wavelength toward the sample, b) measuring at least one of a reflection of the light flux from the sample and a portion of the light flux received via the sample, and c) estimating the number of somatic cells according to the measurement.

According to another aspect of some embodiments of the present invention there is provided a method for acquiring spectrometric information from flowing milk. The method comprises: a) sustaining a light source at a predefined temperature using a heating device, b) using the light source for emitting a light flux toward a flowing milk, the light source having a predefined intensity in the predefined temperature, and c) acquiring a spectrometric measurement from at least one of a reflection of the light flux from the sample and a portion of the light flux received via the flowing milk based on the predefined intensity.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method, the device, and the system of the present invention involves performing or completing certain selected acts manually, automatically, or a combination thereof. Moreover, according to actual instrumentation and equipment of preferred embodiments of the method, the device, and the system of the present invention, several selected acts could be implemented by hardware or by software on any operating system of any firmware or a combination thereof. For example, as hardware, selected acts of the invention could be implemented as a chip or a circuit. As software, selected steps of the invention could be implemented as a plurality of software instructions being executed by a computer using any suitable operating system. In any case, selected acts of the method, the device, and the system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
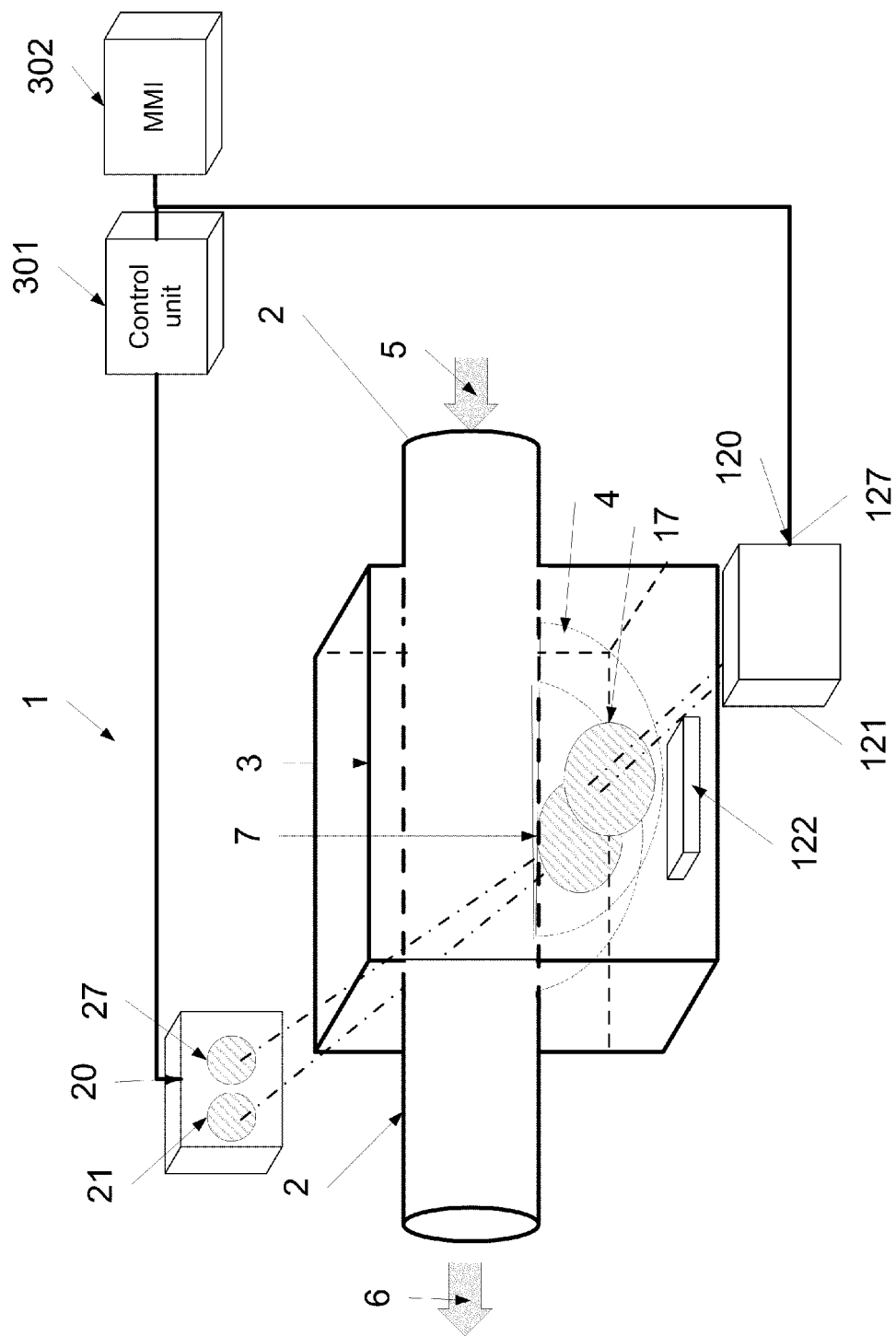
FIG. 1 is a schematic illustration of a spectroscopic milk analyzer having two optic sets, according to one embodiment of the present invention.

Some embodiments of the invention are concerned with an apparatus and method for acquiring spectrometric data from a sample of a flowing fluid, such as milk. An exemplary embodiment comprises at least two light sources, which are designed to illuminate a sample of the flowing fluid. Preferably, each light source includes a set of sources such as LEDs, each having a bandwidth centered on a different wavelength. The various wavelengths are adjusted to allow the measurement of a different component in the sample of the flowing fluid, as described below. The exemplary embodiment further comprises at least two light detectors for measuring the intensity of reflections and/or transmission of the light reflected from and passing through the sample of the flowing fluid and portions of the light that have been reflected and absorbed by the sample of the flowing fluid. Such measurements provide information about one or more components of the probed fluid. For example, if the probed fluid is milk, the information may represent the percentage of fat, total protein, casein, lactose, blood, progesterone, amino-acids urea, and nucleic acid in the sample of the flowing fluid. As further described below, such information may also be used for estimating the number of somatic cells in the milk, especially if it is based on a reflection of a UV light flux from the sample of the probed fluid. The measurements are forwarded to a control unit that generates one or more spectra value according to the measurements. Preferably, the spectra values are used for chemometric analysis of the sample, as further described below.

Some embodiments of the present invention are concerned with an apparatus for acquiring spectrometric information from a sample of flowing fluid that incorporates a thermo-stabilization unit. In these embodiments, the apparatus comprises a light source and a light detector for acquiring spectrometric measurements of the sample of flowing fluid, optionally as described above. The apparatus further comprises a thermo-stabilization unit, for sustaining the light sources at a predefined temperature. By sustaining the temperature of the light sources, thermo-stabilization unit stabilizes the intensity of the light flux on a predefined intensity. Such stabilization improves the robustness of spectra values, which are generated according to the spectrometric measurements.

Some embodiments of the present invention are concerned with an apparatus for acquiring spectrometric information from a sample of flowing fluid that integrates source light calibration unit. In such embodiments, the apparatus comprises a light source and a light detector, optionally as described in the previous embodiments, and a source light calibration unit for calibrating the light emitted by the source during the operation of the apparatus, from a sample of the emitted light as described below.

Some embodiments of the present invention utilize a method for estimating a number of somatic cells in a sample of flowing milk. First, a light flux, which is optionally centered on an ultraviolet (UV) wavelength, illuminates the sample. Then, the intensity of that portion of the light transmitted through the sample and/or optionally the intensity of the portion reflected from the sample is measured. After one or more of the aforementioned measurements have been acquired, the number of somatic cells is estimated based on the measurements. This method allows the estimation of the number of somatic cells in the sample during the milking process, thereby allows the operator to estimate the quality of the flowing milk even before it arrives at the collection point, as described below.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. In addition, it is to be understood that the phraseology and terminology employed herein is for the purpose of description and should not be regarded as limiting.

Reference is now made to FIG. 1, which is a schematic illustration of a spectroscopic milk analyzer 1, according to one embodiment of the present invention. The spectroscopic milk analyzer 1 comprises a portion of a flow conduit 2, optionally tubular 2, that allows fluids, such as milk from a milking station 5 to flow therethrough towards a collection point 6. It should be noted that the milk being transported may be any type of milk such as cow's milk, goat's milk, buffalo's milk, camel's milk and Sheep's milk. The spectroscopic milk analyzer 1 further comprises a sampling chamber 3, which is assembled into the milk flow conduit 2.

The sampling chamber 3 includes a sampling cavity 4 that is designed to contain a sample of the flowing milk. Adjacent to the sampling cavity 4 two opposite optical sets 20, 120, each incorporating a light source 21, 121 are situated. Each of the light sources 21, 121 optionally includes a set of light sources such as a set of discrete LEDs. In some embodiments of the invention, eight LEDs are used, but other numbers of light sources such as organic LED (OLED), a laser diode, or a fluorescent lamp may be used. Each optical set 20, 120 further include a light detecting unit 27, 127, optionally including a set of two or more photo detectors, such as a hybrid UV-optical sensor, analogous to near IR array detectors. Preferably, a Si P-I-N detector array is used. Si PIN detectors, which are operated at very high bias compared to near-IR detectors. Optionally, the light detecting unit 27 includes two detectors having a serial number S5106 of Hamamatsu™, which the specification thereof is incorporated herein by reference.

Detecting units 27, 127 are positioned and oriented to receive light passing through the sample from illumination by the light sources. The optical sets 20, 120 are connected to a control unit 301. The control unit receives the output of the detecting unit and optionally controls the light sources 21, 121, as further described below. Optionally, the spectroscopic milk analyzer 1 comprises a man machine interface (MMI) 302, such as a display and a number of push buttons. Optionally, the MMI allows the user of the spectroscopic milk analyzer 1 to receive indication about the current working mode and the functionality of the spectroscopic milk analyzer 1. Optionally, the MMI comprises a display screen.

In an embodiment of the invention, at least some and usually each of the LEDs of the light sources 21, 121 emits light at a different wavelength within a predefined range to be used for the measurement, as described below. According to one exemplary embodiment, the wavelengths of the LEDs of the light sources 21, 121 range between 360 nm and 970 nm, to cover the UV to near IR regions of the spectrum. In an embodiment of the invention, the spectroscopic milk analyzer 1 is design to illuminate the sample with light in the UV range, preferably between 360 nm and 400 nm, for measuring the number of somatic cells in a milk sample, and light in the near IR range for detecting concentration of protein in a milk sample, as described below.

As further described below, the spectroscopic milk analyzer 1 is designed to perform spectrophotometric analysis to the fluids in the sampling cavity 4 during the milking process. Milk, which is streamed into the flow conduit 2 from the milking station 5, is spectrophotometricaly analyzed using the spectroscopic milk analyzer 1 and then streamed to the collection point 6.

Optionally, each one of the lateral sides of the sampling cavity 4 has a transparent port 7, 17 formed therein. The transparent ports 7, 17 are preferably positioned on a common axis. In an embodiment of the invention, the transparent ports are made of polysulphone (PSU) that optionally coated with an anti-reflection layer. Preferably, the PSU is a virtually entirely transparent (water-clear) PSU. The transparent ports 7, 17 allow light from each of the optical sets 20, 120 to illuminate the fluids in the sampling cavity 4. A portion of the illumination from the light source 21(121) is reflected back to the light detecting unit 27 (127) of the illuminating optical set 20 (120) and a portion is transmitted to the opposite detecting unit 127 (27) of the opposite illuminating optical set 120 (20). Thus, in an embodiment of the invention, a light detecting unit of a certain optical set, for example 27, is designed to intercept light emitted from the light source 121 of the opposite optical set 120 and reflections of the neighboring light source 21. In this embodiment, the same light detecting unit is used for outputting measurements which are based on the light reflected from the fluids in the sampling cavity 4, and measurements which are based on the light that has passed via the fluids in the sampling cavity 4.

As described above, the light detecting units 27, 127 are used to outputting measurements which are based on the light reflected from the fluids. Such measurements may be affected from light that is reflected from the surface of the transparent port that is positioned in front of the respective optical set 20, 120. In order reduce or eliminate the effect of such surface reflections, the transparent ports 7, 17 are preferably angled in acute angle relative to the plane of the detecting unit. Optionally, the transparent ports 7 are position in an acute angle relative to the housing of the spectroscopic milk analyzer 1, thereby allowing the detecting units 27, 127, to receive reflections from the probed fluid without reflections from the surface of the transparent ports 7, 17.

Optionally, the spectroscopic milk analyzer 1 further comprises a scattering detecting unit 122, which is designed for receiving light scattered from the probed fluid. The direction, frequency, or polarization of a light flux is changed when it interacts with the components of the fluid. By measuring the scattered light, the scattering detecting unit 122 may produce measurements, which are indicative to the concentrations of certain components in the fluid. For example, the in milk light is scattered mostly at the tiny fat droplets in the sample.

The spectrophotometric analysis is based, inter alia, on measurements of the reflectance of the light flux emitted by the LEDs of the light sources 21, 121 from the sample of the portion in the sampling cavity 4, which may be referred to as a reflected light flux. The light detecting unit 27, 127 of the illuminating optical set 20, 121 measures such the aforementioned reflectance. The spectra values, which are based on the aforementioned reflectance, may be used, for example, to determine fat content in milk using light in the near infrared range, see Schmilovich, Z. et al., Near Infrared Spectroscopy of Milk in its Heterogeneous State, Comp. Elec. Agric. 29:195-207, which is incorporated herein by reference.

The spectrophotometric analysis is further based on the intensity of light flux transmitted through the fluids in the sampling cavity 4, and measured by the light detectors 127 (27) of the opposite optical set 120 (20). The spectra values, which are based on the transmission measurements, can be used to indicate the absorption and optionally the scatter of the emitted light at various wavelengths by one or more components of the probed fluids. Such spectra values may be used in quantitative analysis of the certain components. For example, a calibration equation, which is made by a chemometric technique such as multiple linear regression (MLR), principal component regression (PCR), and Partial Least Squares (PLS) regression, is used for prediction of components in the milk based on NIR spectra of unhomogenized milk, see, for example, V. Pravdova et al., Calibration of SCC in milk based on NIR spectroscopy, Anal. Chim. Acta, 450, 131-141 (2001), which is incorporated herein by reference.

Optionally, the spectra values, which are based on such the aforementioned measurements, are calculated in relation to a calibration intensity that has been measured by the spectroscopic milk analyzer 1 during the calibration thereof. The calibration intensity is preferably calculated using a calibration fluid. Preferably, the spectroscopic milk analyzer 1 is calibrated before it is positioned in the cowshed. As described above, in one embodiment of the present invention the fluid is milk, such as cow milk. In this embodiment, during the calibration fluid is optionally ultra-high temperature processing (UHT) milk having one percent fat.

As commonly known, milk from the milking station 5 is received in batches. Each one of the batches may be probed by the spectroscopic milk analyzer 1, as further described below. The sampling cavity 4, which preferably has a semicircular shape, as shown in FIG. 1, is designed to allow a continuous flow of fluids from the milking station 5 to the collection point 6. A detailed description of the sampling chamber 3, sampling cavity 4, and the continuous flow of fluids from the milking station 5 to the collection point 6 via the sampling chamber 3 is provided in FIG. 1, FIG. 3A, and FIG. 3B and the related description in International Patent Publication No. WO/2003/040704, which is incorporated herein by reference.

In use, a sample of fluids that is currently in the sampling cavity 4 is substantially replaced with a new sample from a new portion that is received from the milking station 5 via the conduit 2. Thus, there is a separation between the probed portions and each portion is analyzed separately. The sampling cavity 4 allows the air in the sample taken from a received portion to dissolve. Preferably, the sampling cavity 4 comprises a solenoid (not shown) for identifying whether there is a sample in the sampling cavity 4 or not and to identify new samples.

Figure 2:
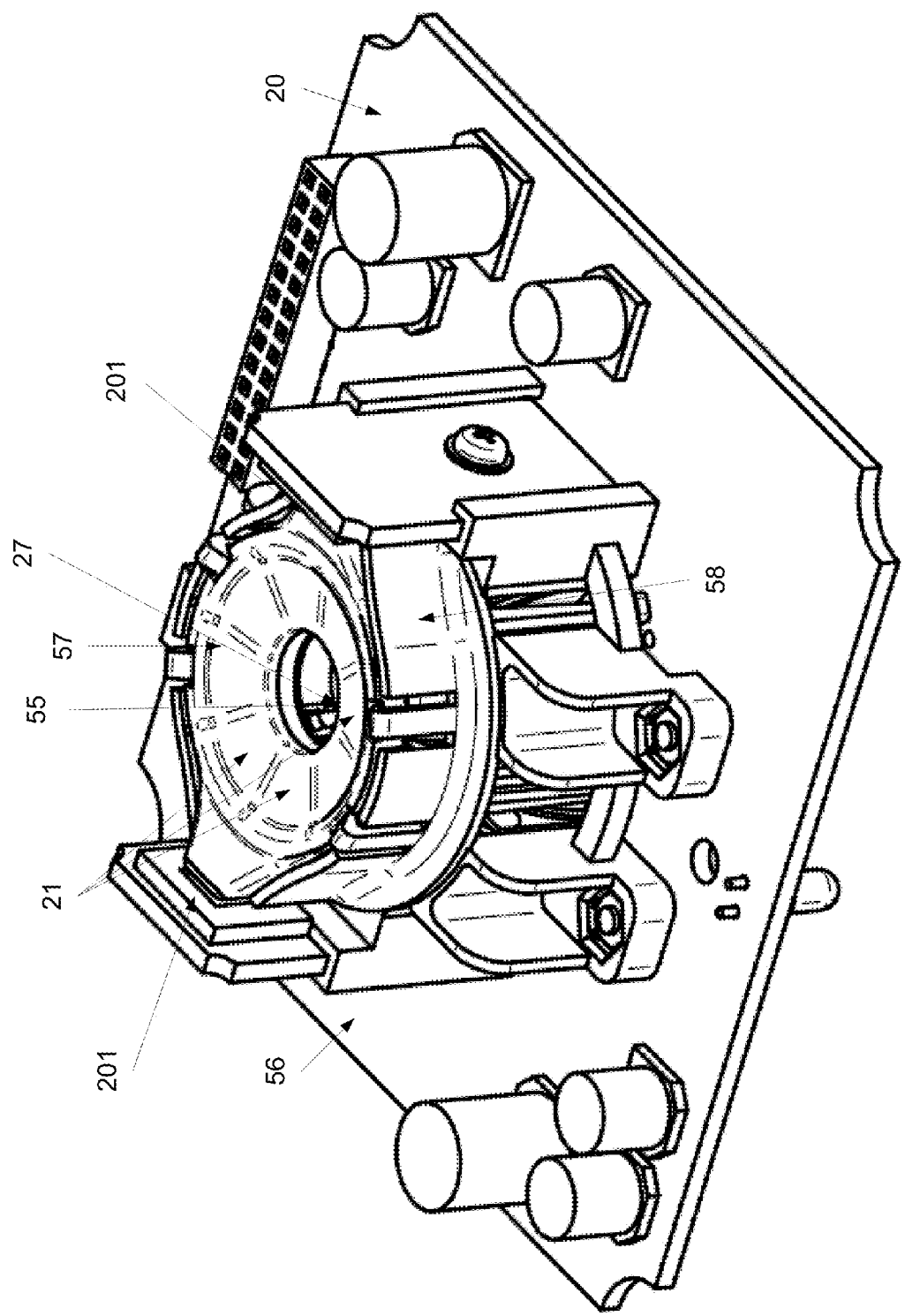
FIG. 2 is a schematic illustration of an exemplary optical set, which is installed on an integrated circuit (IC) board and comprises a light source and a light detecting unit, according to one embodiment of the present invention.

Reference is now made to FIG. 2, which is schematic illustration of an exemplary optical set 20, according to one preferred embodiment of the present invention. As described above, the optical set 20, which is optionally installed on an integrated circuit (IC) board, comprises the light source that includes a set of LEDs 21 and the light detecting unit 27. FIG. 2 further depicts two optional parallel feedback detectors 201, a protective housing 58 that encircles the light source 21 and the light detecting unit 27, and a transparent plate 57, which is positioned in front of the LEDs of the light source 21 and the light-detecting units 27. Optionally, the transparent plate 57 is designed to function as a guide light and to direct a portion of light emitted from the LEDs of the light source 21 toward one or both of the feedback detectors 201, as further described below.

Optionally, a converging lens 55 is positioned in front of the light detecting unit 27 converging light received from the opposite source or reflected from the liquid, through the transparent plate, which is positioned in front of the optical set 20.

Figure 3:
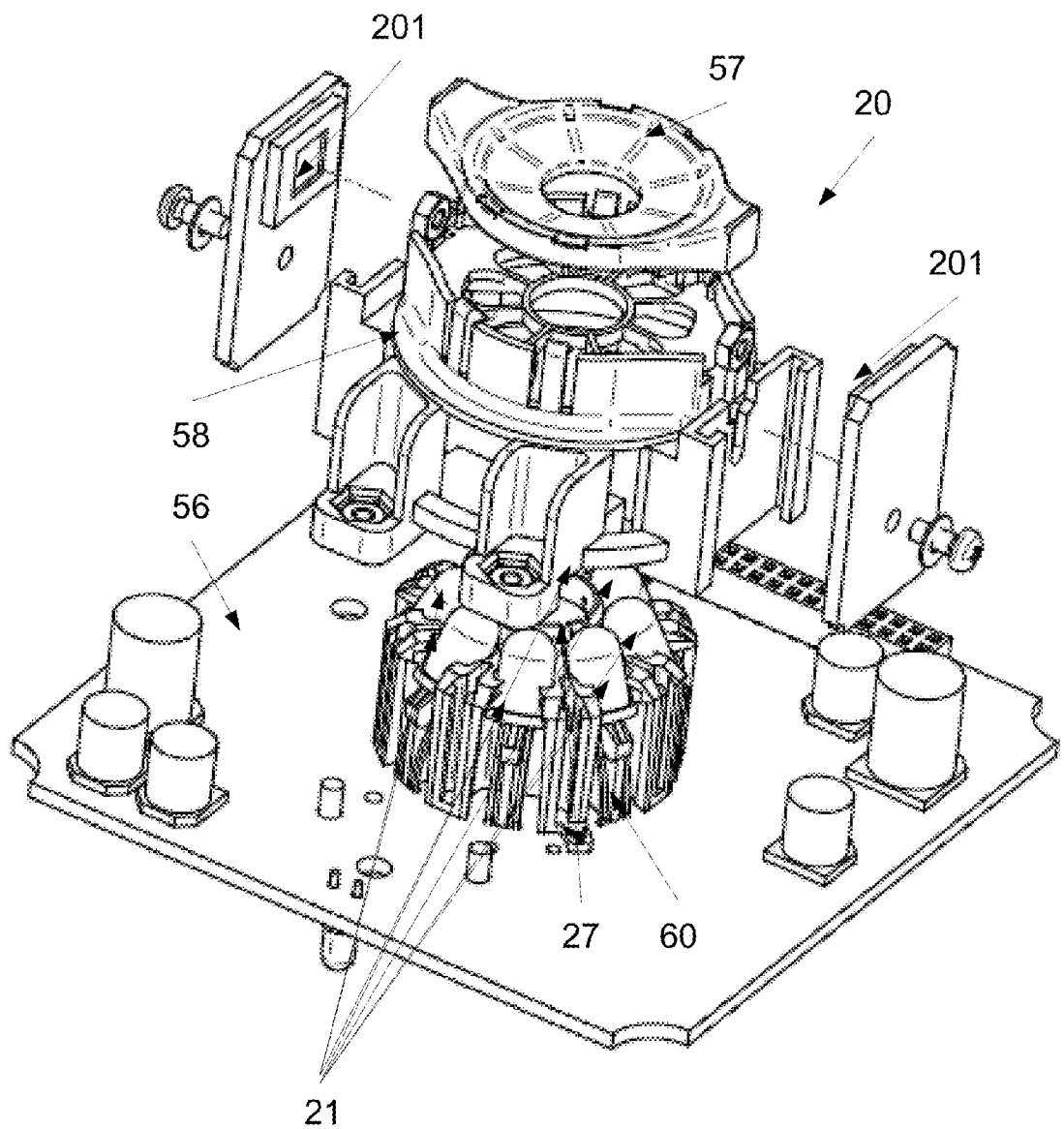
FIG. 3 is schematic illustration of the exemplary optical set of FIG. 2, wherein some of the components of the exemplary optical set are depicted in separate from one another.

Reference is now also made to FIG. 3, which is partially exploded schematic illustration of the exemplary optical set 20 depicted in FIG. 2. As depicted in FIG. 3, the LEDs of the light source 21 are positioned on a carrier 60 that engages them in a circle. Each one of the LEDs of the light source 21 is engaged with an inclination toward the center of the circle. In such a manner, the light flux, which is emitted from each one of the LEDs of the light source 21, directly illuminates the near transparent port of the sampling cavity, as described below.

The configuration of the LEDs of light source 21, as shown in FIG. 3, reduces the space needed for such a set of LEDs and allows the positioning of two optical sets facing each other, as depicted in FIGS. 2 and 3. The positioning of such optical sets across from each other reduces the space needed for allowing such a large set of LEDs to illuminate the fluid in the sampling cavity 4. Please refer to FIG. 4 and related text for more details.

Reference is now made, once again, to FIG. 1. Optionally, the LEDs of the light source 21, 121 of a certain optical set 20 or 120, are activated in a sequential manner. The LEDs of the light sources 21, 121 are preferably activated one after the other in different illumination cycles. During each illumination cycle, a light flux with a different wavelength is emitted by one of the LEDs in one of the light sources 21, 121 toward the respective transparent plates 7, 17, for example, as described above. As described above, the LEDs of the light sources 21, 121 illuminate the fluids in the sampling chamber 3 with light fluxes centered on wavelengths between 360 nm and 970 nm. The LEDs of the light sources 21, 121 comprises LEDs such as aluminum gallium arsenide (AlGaAs) LED, aluminum gallium phosphide (AlGaP) LED, aluminum gallium indium phosphide (AlGaInP) LED, gallium arsenide phosphide (GaAsP) LED, gallium phosphide (GaP) LED, gallium nitride (GaN), indium GaN (InGaN), silicon carbide (SiC) LED, silicon (Si) LED, sapphire (Al2O3) LED, zinc selenide LED, diamond (C)—LED, aluminum nitride (AlN) LED, and aluminum gallium nitride (AlGaN) LED.

In one embodiment of the present invention, the spectroscopic milk analyzer 1 is used for measuring the presence of somatic cells in the fluid, which is optionally milk. In such an embodiment, the presence of somatic cells is detected by measuring the intensity of reflected or transmitted light flux that is centered at UV wavelength, preferably between 365 nm and 400 nm. The spectra value, which is based on the detected intensity, is substituted in a mathematical model for chemometric analysis and the output of the chemometric analysis is used for choosing a value that represents an estimated number of somatic cells in the sample of the milk. Optionally, the mathematical model is defined as follows:

$$\text{somatic cells count (SCC)} = K_1 S_{i_1} + K_2 S_{i_2} + \ldots + K_n S_{i_n}$$

wherein n denotes the number of illumination cycles, $K_n$ denotes a model coefficient representative of an MLR process that has been performed according to the n illumination cycles, and $S_{i_n}$ denotes the spectra value that has been measured by a respective illumination cycle.

Optionally, the presence of somatic cells is divided to a number of presence levels; each level represents a different quota of somatic cells.

A sample of each batch of milk fills the sampling cavity 4 and illuminated sequentially by all the LEDs of the optical sets 120, 20. Preferably, each one of the LEDs of both the light sources 21, 121 emits light in a different range of wavelengths. In one embodiment of the present invention, 16 LEDs each with a different range of wavelengths (8 in each one of the optical sets 120, 20), sequentially illuminate the fluids in the sampling cavity 4 in a 16 stage illumination cycle. During each illumination cycle, measurements, such as the intensity and the frequency of both the light flux that is reflected from the fluids and the light flux that has been passed through the fluids are measured. In such a manner, 32 measurements are provided to the control unit 301, as described below. In a specific embodiment of the invention LEDs of the light sources 21, 121 are fed with 80 mA of load current and designed to work in rapid power-on cycles of 70 milliseconds each.

In each one of the illumination cycles, the acquisition of signals from light detecting units 127, 27 of the optical sets 120, 20 is coordinated with the wavelength of the emitted light. Each one of the light detecting units 27, 127 analyzes the received light flux and generates an intensity signal corresponding to the intensity of the detected light flux. Preferably, the intensity signals are digitized before processing using analog-to-digital (AD) IC.

The intensity signals from the light detecting units 27, 127 are preferably amplified and processed, optionally by a common processing unit. The intensity signals are preferably forwarded to the control unit 301, where the spectrum of the transmitted and/or reflected light is obtained and analyzed. Preferably, the control unit 301 calculates a spectrum value for each one of the light detecting units 27, 127 in each one of the illumination cycles of each one of the LEDs. Optionally, the spectra value is based on the differences between the intensity signal that has been generated in response to a certain reflected light flux or a certain passing light flux with an intensity signal that has been generated when the fluids have not been illuminated and the light sources 21, 121 have been inactive. Preferably, if one or more of the spectra values are above or below a certain quality factor, the sampling is disqualified and the other spectra values are preferably not assessed. Such an embodiment allows, inter alia, the disqualification of a sample that has been contaminated by air. Preferably, for each portion, 32 intensity signals are generated in 16 illumination cycles, as described above, and 32 spectra values are calculated based thereupon. Optionally, the intensity of the emitted light is calibrated, as further described below.

The spectra values of the spectroscopic milk analyzer 1 are preferably forwarded to a central computing unit. The central computing unit analyzes the spectra values and output a report, a status notice, or an alert. Preferably, all the spectra values are used as parameters in a mathematical model, such as a polynomial expression or any other application of statistical and methods to chemic analysis. The output of the mathematical model reflects the concentration of predefined components in the fluids. Optionally, the control unit 301 performs the analysis of spectra values. Optionally, the control unit 301 calibrates the mathematical model before it produces the report. Optionally, the calibration of the models was performed using a partial least squares (PLS) regression technique. The calibration allows the use of inexpensive LEDs non-uniform wide spectral range.

Optionally, the aforementioned MMI, which is depicted in FIG. 1 displays the outcomes of the analysis. Optionally, if one or more of the spectra values are in a predefined abnormality range, the spectroscopic milk analyzer 1 is malfunctioning, or the connection with the central computing unit has been disconnected, the MMI displays an alarm.

As described above, optionally the analyzed fluids are milk. Preferably, the spectra values are used for evaluating the concentration of the various component parts of the milk. These components include fat, total protein, casein, lactose, somatic cells, blood, progesterone, amino-acids urea, and nucleic acid. Such information is important for evaluating the quality and the toxicity of the milk, as described above.

Preferably, the spectra values are compared with predefined default spectra values, which are obtained in an analysis of similar milk in laboratory conditions, for example, using a MilkoScan™ FT2 of FOSS™. In such an embodiment, spectra values of cow's milk are compared with predefined default spectra values of cow's milk and spectra values of goat's milk are compared with predefined default spectra values of goat's milk.

Preferably, the default spectra values are ranges, which are determined, inter alia, according to the estimated accuracy of the spectra values.

Optionally, the control unit 301 controls the switching order and the activation timing of the LEDs of the light source 21, 121, for scanning the complete spectral range to be measured. Preferably, the aforementioned illumination cycles take place seriatim, one after another, during the milking process.

As described above, according to one preferred scanning program, each one of the LEDs of the light sources 21, 121 is turned on for several milliseconds, preferably 70 milliseconds, and the absorption and scattering measurements are performed at that wavelength. Preferably, the aforementioned light detecting unit 27, 127 measures received light simultaneously.

A detailed description of the light analysis, which may be performed by the aforementioned light detecting unit 27, 127, is described in International Patent Publication No. WO/2003/040704, which is incorporated herein by reference.

As described above, the fluids in the sampling chamber are spectroscopically analyzed by the spectroscopic milk analyzer 1. As commonly known, the spectroscopic analysis is based on the intensity of the light reflected from or passed through the fluids in the sampling cavity 4. The intensity is measured in relation to values, which are based on the assumption that the fluids in the sampling cavity 4 have been illuminated with a light flux at a predefined intensity, which may be understood as a range of intensities.

Thus, in order to ensure that the analyzed reflections and transmissions are measured properly, the light emitted from the LEDs of the light source 21 should have the predefined intensity. However, as the LEDs of the light source 21 may be activated and functional for long periods, they may have to be calibrated from time to time in order to ensure that the actual intensity of the emitted light is in the predefined intensity. The calibration may be an automatic self-calibration.

Preferably, the spectroscopic milk analyzer comprises a LED calibration unit (not shown). As depicted in FIG. 3, each one of the optical sets comprises one or more feedback detectors 201, which are preferably connected to the LED calibration unit and designed to intercept a portion of the direct light flux, which is generated by the LEDs of the light source 21. Preferably, the intercepted portion is used for monitoring the intensity of light emitted by the LEDs.

Figure 4:
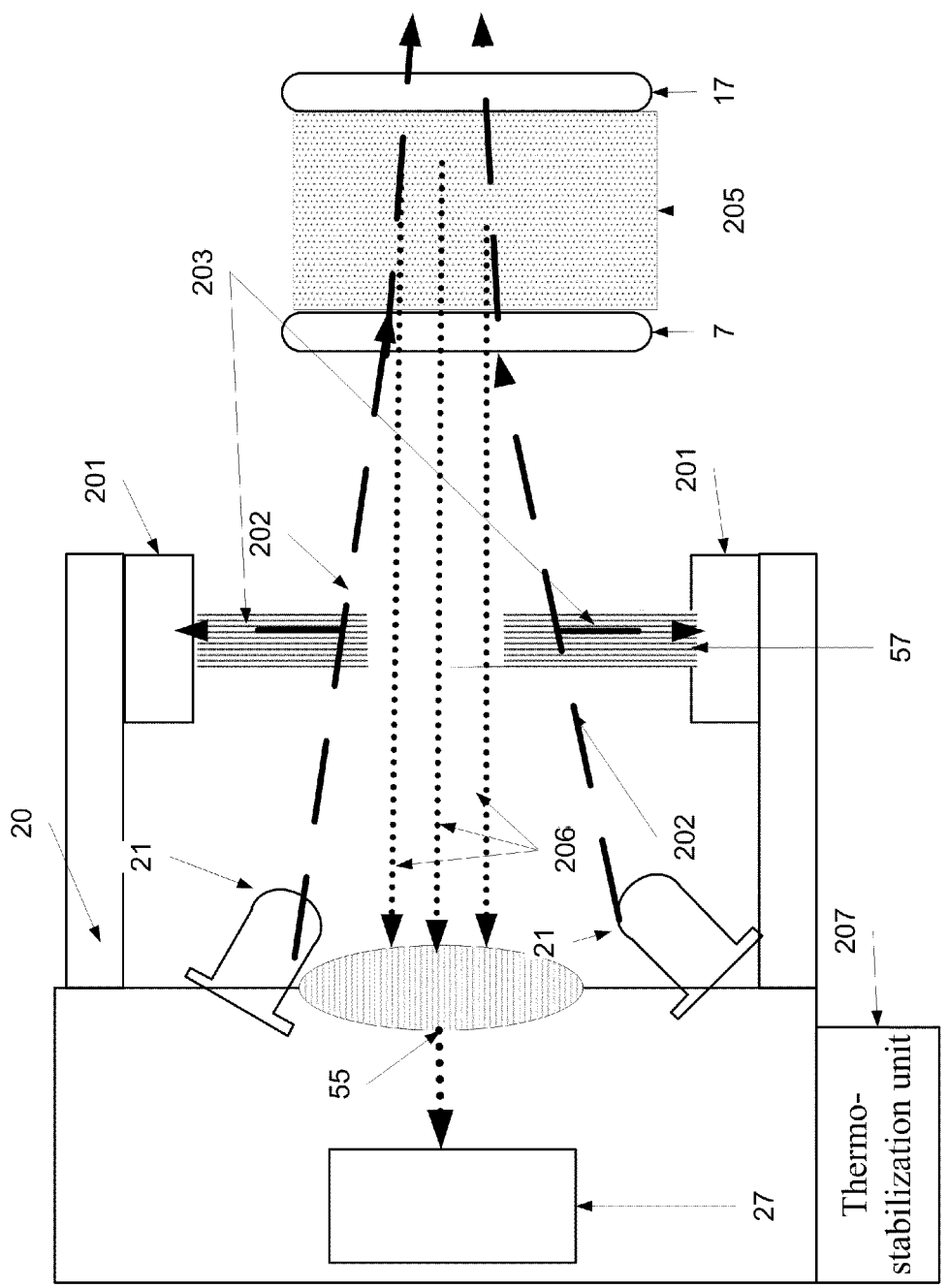
FIG. 4 is a sectional illustration of an optical set, which is described in FIG. 2, according to some embodiments of the present invention.

Reference is now made to FIG. 4, which is a sectional illustration of the optical set 21, which is described in FIG. 2, according to one embodiment of the present invention. The feedback detectors 201, which are attached to the optic set 20, are designed to receive a portion of the light flux 202 that is emitted from the LEDs of the light source 21, while another portion of the light flux 202 is directed toward the transparent plate 7. Optionally, the light guide 57 derives a portion of the light flux 202 that is emitted from the LEDs toward the feedback detectors 201, as shown at 204. The derived portion is preferably taken from the center of the light flux 202. In such a manner, the portion reflects the actual intensity of the light flux 202 that illuminates the sample 205.

The intensity of the intercepted portion of the light flux 202 is measured and forwarded to the LED calibration unit. The LED calibration unit performs an intensity analysis and verifies that the intensity of the portion of the light flux 202 is in the predefined intensity, which preferably has been defined during an initial calibration of the optical set 20. Preferably, the intensity analysis is performed every predefined period, preferably 2 minutes. Optionally, the calibration is performed when the light detecting unit 27 is inactive. Preferably, the LED calibration unit generates a correction signal that is sent to the control unit that controls, inter alia, the intensity of the LEDs of the light source 21. The control unit adjusts the intensity of the LEDs of the light source 21 according to the correction signal, thereby ensures that the probed fluids are illuminated with a light flux 202 that is tuned according to the predefined intensity. Preferably, the power of current remains unchanged during the calibration process.

In one preferred embodiment of the present invention, the optic sets 20, 120 of the spectroscopic milk analyzer comprise an optional thermo-stabilization unit 207 (not shown). Thermo-stabilization unit 207, which is preferably fabricated on the IC of the optic set, is designed to maintain the working temperature of the LED in a fixed range of working temperatures.

One of the factors that have an influence on the performances of LEDs of the light source 21 is the working temperature. The heat generated in the course of the operation of the light-emitting elements of the LED is not completely dissipated and therefore gradually raises the temperature of the entire LED. Such a heating has an effect on the stability of the intensity of the emitted light flux. Usually, the higher is the temperature, the lower is the intensity of the emitted light flux. The spectroscopic milk analyzer, which is preferably designed to be installed in cowsheds and a like, may have to operate efficiently in a working temperature that ranges between 5° C. and 40° C. In order to ensure that the light emitted from the LEDs of the light source 21 remains constant in such a range of temperatures, thermo-stabilization unit 207 is designed for stabilizing the temperature of the LEDs of the light source 21 in a predefined range. As the estimated working temperature in an average cowshed ranges between 5° C. and 40° C. and the estimated heat increment, which is caused by the electronic components of the spectroscopic milk analyzer, ranges between 10° C. and 12° C., thermo-stabilization unit 207 is designed for stabilizing the temperature of the LEDs of the light source 21 at around 50° C. Preferably, thermo-stabilization unit 207 comprises a temperature sensor, a control unit, and a set of heating resistors. Preferably, each thermo-stabilization unit 207 comprises a set of 14 parallel heating resistors, 14 sensors, and a proportional-integral (PI) controller. The PI controller output a correction to the deviation between the temperatures measured by thermometer and a predefined range of temperatures, preferably around 50° C., by calculating and then outputting a correction signal to the set of heating resistors. Preferably, the resistance of each one of the heating resistors is approximately 1.5KΩ. Preferably, each heating resistor receives 24V current. Preferably, thermo-stabilization unit 207 keeps the temperature in the predefined range when the spectroscopic milk analyzer 1 is operative and when it is idle. Such a temperature may assist in preventing ingress of water and humidity into the spectroscopic milk analyzer 1. The relatively high temperature reduces the humidity inside the spectroscopic milk analyzer 1, thereby improves the clearness of the transparent plate and the converging lens. Such an improvement increases the accuracy of the intensity measurement.

Figure 5:
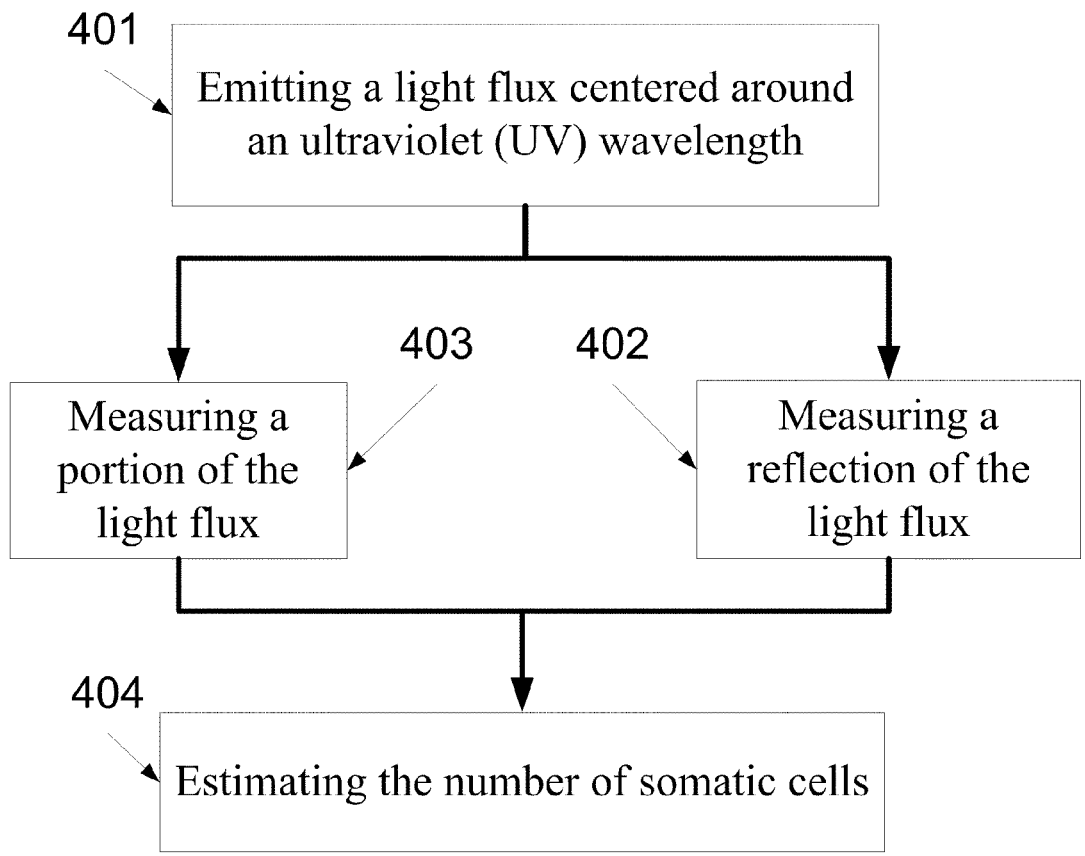
FIG. 5 is a flowchart of a method for estimating a number of somatic cells in a sample of flowing milk, according to some embodiments of the present invention.

Reference is now made to FIG. 5, which is a flowchart of a method for estimating a number of somatic cells in a sample of flowing milk, according to an embodiment of the present invention. As described above, the present invention discloses a spectroscopic milk analyzer, which is designed to measure the reflectance of light fluxes, which are centered on different wavelengths, from a sample of flowing milk. The spectroscopic milk analyzer is further designed to measure the intensity of portions of the light fluxes, which are passed via the sample of flowing milk, as described above. Such ability may be used, for estimating the number of somatic cells in the flowing milk. First, as indicated at 401, a light flux that is centered on an ultraviolet (UV) wavelength is emitted toward the sample. Then, as indicated at 402, the intensity of a portion of the light flux that has been received via the sample or preferably of the intensity of a reflection of the light flux is measured. Now, after one or more of the aforementioned measurements have been acquired, the number of somatic cells is estimated accordingly, as indicated at 403. This allows, inter alia, the estimation of the number of somatic cells in the flowing milk even before it arrives at the collection point, as described above. The counted number of somatic cells is important in order to estimate the quality and the marketability of the probed milk. The presence of other components, such as protein and urea, in the probed fluid may also be estimated according to the aforementioned measurements.

It is expected that during the life of this patent many relevant devices and systems will be developed and the scope of the terms herein, particularly of the terms a heating resistor, a control unit, a LED, and an IC are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A spectrometric sensor for measuring a spectra value of a sample of flowing milk, said spectrometric sensor comprising:
   a sampling chamber for containing a sample of flowing milk;
   a light source for emitting a first light flux toward said sample in said sampling chamber;
   a light detector for measuring a first intensity of a reflection of said first light flux from said sample and for measuring a second intensity of a second light flux transmitted through said sample;
   a light calibration unit for receiving a portion of said first light flux that does not enter said sampling chamber and adjusting said light source to emit light at a predefined intensity; and
   a control unit for calculating at least one spectra value according to at least one of said first and second intensities and performing an analysis of said sample according to said at least one spectra value.

2. The spectrometric sensor of claim 1, wherein said first light flux is an ultraviolet light flux centered at an ultraviolet wavelength.

3. The spectrometric sensor of claim 1, wherein said control unit is configured for calculating a concentration of somatic cells in said sample according to said analysis.

4. The spectrometric sensor of claim 1, wherein said light calibration unit comprises a feedback detector for receiving said portion of said first light flux.

5. The spectrometric sensor of claim 4, wherein said portion of first light flux is guided to said feedback detector by a light guide.

6. The spectrometric sensor of claim 5, wherein said light guide derives said portion of first light flux from approximately the center of said first light flux.

7. The spectrometric sensor of claim 1, further comprising a converging lens for converging said reflection and said second light flux onto said light detector.

8. The spectrometric sensor of claim 1, wherein said analysis is a chemometric analysis, said control unit comprises a central unit and a local unit said local unit transmitting said at least one spectra value to said central unit for performing said chemometric analysis.

9. The spectrometric sensor of claim 8, wherein said sampling chamber having first and second transparent portions, said first and second light fluxes being respectively emitted toward said first and second transparent portion.

10. The spectrometric sensor of claim 1, wherein said sampling chamber is assembled into a milk flow conduit.

11. The spectrometric sensor of claim 1 further comprising a thermo-stabilization unit for sustaining said light source in a predefined temperature range, thereby stabilizing said light flux at a predefined intensity.

12. The spectrometric sensor of claim 11, wherein said thermo-stabilization unit comprising a heating device, said sustaining being performed using said heating device.

13. The spectrometric sensor of claim 1, wherein said light source comprises a set of light emitting diodes (LEDs) for emitting a plurality of first light fluxes, said light detector being configured for measuring a plurality of intensities of at least one of reflections of said plurality of first light fluxes from said sample and a plurality of second light fluxes received via said sample, said control unit generating said at least one spectra value according to said plurality of intensities.

14. The spectrometric sensor of claim 13, wherein each said LED generates light at a band of wavelengths centered at a different wavelength from the other LEDs.

15. The spectrometric sensor of claim 1, wherein said light detector is configured for measuring calibration intensity from at least one of a reflection of said first light flux from a calibration fluid and a portion of said second light flux, said control unit calculating said at least one spectra value according to a deviation between said at least one of said first and second intensities and a calibration intensity.

16. A device for generating one or more spectra values from a sample of flowing milk comprising
 a first spectrometric sensor according to claim 1 comprising a control unit, said device further comprising an additional spectrometric sensor comprising:
 a additional light source for emitting said second light flux toward said sample; and
 a additional light detector for measuring a third intensity of a reflection of said second light flux from said sample and a fourth intensity of said first light flux transmitted through said sample
 wherein said control unit further calculates at least one additional spectra value according to at least one of said third and fourth intensities and performing said analysis according to said at least one additional spectra value.

17. A device for measuring an intensity of at least one light flux, comprising:
 a light source for emitting a first light flux having a predefined intensity toward a sample of flowing milk;
 a light detector for measuring a first intensity of a reflection of said first light flux from said sample and for measuring a second intensity of a second light flux transmitted through said sample;
 a light calibration unit for receiving a portion of said first light flux that does not enter said sample and adjusting said light source to emit light at a predefined intensity; and
 a thermo-stabilization unit for sustaining said light source in a predefined temperature range , thereby stabilizing said first light flux at said predefined intensity.

18. A system for estimating a number of somatic cells in a sample of milk, said system comprising:
 a light source for emitting a light flux centered on an ultraviolet (UV) wavelength toward a sample of flowing milk;
 a light detector for measuring a first intensity of a reflection of said first light flux from said sample and for measuring a second intensity of a second light flux transmitted through said sample;
 a light calibration unit for receiving a portion of said first light flux that does not enter said sample and adjusting said light source to emit light at a predefined intensity; and
 a control unit for estimating the number of somatic cells according to said measurement.

19. The system of claim 18, further comprising a sampling chamber for containing said sample.

20. The system of claim 18, wherein the center UV wavelength is between 365 nanometer and 400 nm nanometer.

21. A method for estimating a number of somatic cells in a sample of milk, said method comprising:
 a) emitting a first light flux centered on an ultraviolet (UV) wavelength toward a sample of flowing milk;
 b) measuring a first intensity of a reflection of said first light flux from said sample and a second intensity of a second light flux transmitted through said sample;
 c) calibrating said light flux according to a portion of said first light flux that does not enter said sample; and
 d) estimating the number of somatic cells in the sample of milk according to said at least one of said first and second intensities.

22. A method for acquiring spectrometric information from a flowing milk, said method comprising:
 a) sustaining a light source at a predefined temperature using a heating device;
 b) using said light source for emitting a light flux toward a flowing milk, said light source having a predefined intensity at said predefined temperature;
 c) calibrating and adjusting said light source according to a portion of said light flux that does not enter said milk;
 d) acquiring at least one spectra value from at least one of a reflection of said light flux from said sample and a portion of said light flux received via said flowing milk based on said predefined intensity; and
 d) performing an analysis of said sample according to said at least one spectra value.

* * * * *